United States Patent
Neumann et al.

(10) Patent No.: US 11,434,516 B2
(45) Date of Patent: Sep. 6, 2022

(54) RAPID CULTURE FREE PATHOGEN DETECTION VIA SPECTRALLY RESOLVED FLUORESCENCE MICROSCOPY

(71) Applicants: STC.UNM, Albuquerque, NM (US); NATIONAL TECHNOLOGY & ENGINEERING SOLUTIONS OF SANDIA, LLC, Albuquerque, NM (US)

(72) Inventors: Aaron Kurt Neumann, Albuquerque, NM (US); Matthew S Graus, Albuquerque, NM (US); Jerilyn A Timlin, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 161 days.

(21) Appl. No.: 16/333,665

(22) PCT Filed: Sep. 18, 2017

(86) PCT No.: PCT/US2017/052032
§ 371 (c)(1),
(2) Date: Mar. 15, 2019

(87) PCT Pub. No.: WO2018/053411
PCT Pub. Date: Mar. 22, 2018

(65) Prior Publication Data
US 2019/0292579 A1    Sep. 26, 2019

Related U.S. Application Data

(60) Provisional application No. 62/395,424, filed on Sep. 16, 2016.

(51) Int. Cl.
*C12Q 1/04* (2006.01)
*G01N 21/64* (2006.01)
*C12N 1/16* (2006.01)

(52) U.S. Cl.
CPC ............ *C12Q 1/04* (2013.01); *C12N 1/16* (2013.01); *G01N 21/64* (2013.01); *G01N 21/6458* (2013.01); *G01N 21/6486* (2013.01); *G01N 2021/6423* (2013.01); *G01N 2333/40* (2013.01); *G01N 2800/26* (2013.01)

(58) Field of Classification Search
CPC . C12Q 1/04; C12N 1/16; G01N 21/64; G01N 21/6458; G01N 21/6486; G01N 2021/6423; G01N 2333/40; G01N 2800/26
USPC ............................................. 435/34
See application file for complete search history.

(56) References Cited

U.S. PATENT DOCUMENTS

2015/0148705 A1\*  5/2015  Baym ................. C12Q 1/04
600/572

OTHER PUBLICATIONS

Kang et al., Rapid detection of single bacteria in unprocessed blood using Integrated Comprehensive Droplet Digital Detection, Nature Communications, (2014), pp. 1-10.\*
Patino et al., Autofluorescence of Mycobacteria as a Tool for Detection of *Mycobacterium tuberculosis*, Journal of Clinical Microbiology, vol. 46, No. 10, (Oct. 2008), p. 3296-3302.\*
Kang et al., Rapid detection of single bacteria in unprocessed blood using Integrated Comprehensive Droplet Digital Detection, Nature Communications, (2014), 5: 5427, pp. 1-10.\*
Merriam-Webster.com, Definition of deconvolution, Accessed Oct. 19, 2021, Available online at: www.merriam-webster.com/dictionary/deconvolution.\*
Wong et al., Bayesian-based deconvolution fluorescence microscopy using dynamically updated nonstationary expectation estimates, Scientific Reports, (Jun. 8, 2015), pp. 1-9.\*
Spectral Imaging and Linear Unmixing, Nikon Instruments, Inc. 2021.

\* cited by examiner

*Primary Examiner* — Jennifer M. H. Tichy
(74) *Attorney, Agent, or Firm* — Gonzales Patent Services; Ellen M. Gonzales (57) ABSTRACT

Methods and apparatus for rapid, culture free pathogen detection. The methods utilize optical spectroscopy techniques to identify and/or characterize pathogens in a sample via the detection of unique properties and/or analytes that are specific to particular pathogens.

15 Claims, 7 Drawing Sheets

| Pruning Level/ Number of Nodes | Resubstitution Error (Training Set) | Cross Validation Error (Training Set) | True Predictive Error (Test Set) | Accuracy (Test Set) |
|---|---|---|---|---|
| Full Tree/21 | 0.0979 | 0.2374 | 0.2703 | 72.97 |
| Level 1/19 | 0.1009 | 0.2136 | 0.2432 | 75.68 |
| Level 2/17 | 0.1068 | 0.2522 | 0.1892 | 81.08 |
| Level 3/15 | 0.1157 | 0.2315 | 0.1622 | 83.78 |
| Level 4/12 | 0.1306 | 0.2344 | 0.1622 | 83.78 |
| Level 5/7 | 0.1602 | 0.2315 | 0.1622 | 83.78 |
| Level 6/4 | 0.1929 | 0.2404 | 0.1622 | 83.78 |

RAPID CULTURE FREE PATHOGEN DETECTION VIA SPECTRALLY RESOLVED FLUORESCENCE MICROSCOPY

CROSS-REFERENCE TO RELATED APPLICATIONS

The following application claims benefit of U.S. Provisional Application No. 62/395,424, filed Sep. 16, 2016, which is hereby incorporated by reference in its entirety.

STATEMENT REGARDING GOVERNMENT SPONSORED RESEARCH

This invention was made with Government support under Contract No. DE-NA0003525 awarded by the United States Department of Energy/National Nuclear Security Administration. The Government has certain rights in the invention.

BACKGROUND

There is an urgent need for rapid, culture-free diagnostics for infectious disease. Most diagnostic methods are hampered by the need for a microbiological culture step, which causes a delay of at least 24-48 hours before the organism is identified. In patients with septic shock, significant immune compromise and meningitis, treatment delay is unacceptable as it leads to high mortality. These patients require initiation of antimicrobial therapy within hours. At present, empiric antimicrobial therapy is provided well before the pathogen is known. Rapid identification (i.e., within hours) of even the general class of pathogen would direct therapy toward an appropriate target at an earlier stage, save lives and improve health outcomes.

As a specific example, cancer patients receiving cytotoxic antineoplastic therapies are at high risk for infection due to neutropenic status, which compromises innate immune inflammatory responses, and frequent occurrence of mucositis, which allows translocation of pathogens across mucosal surfaces. 70% of these patients require emergent care and ~23% of those present with fever/febrile neutropenia[12,15]. Empiric antimicrobial therapy should be initiated within an hour of triage, and each hour of delay is associated with an 18% increase in mortality[3,14]. *Pseudomonas aeruginosa, Staphylococcus aureus* and *Candida albicans* are all common causes of febrile neutropenia, each requiring different antibiotics for appropriate coverage.

*Candida* species are commensal pathogens that usually reside on mucosal surfaces. If given the opportunity, the fungus will transition from a commensal organism to become a pathogen which can create infections that range from superficial to systemic. *Candida* species are the most common fungal pathogens with *C. albicans* arising the most often followed by *C. glabrata* and *C. parapsilosis*, respectively[1,2,3,4]. Not only is there a high mortality rate associated with candidiasis, but there is also a healthcare cost that can exceed billions of dollars annually[1,5,6,7].

In order to reduce mortality associated with fungal infections, early and accurate identification are essential. Studies have shown that late diagnosis and incorrect diagnosis of *Candida* species leads to a significant increase in mortality[8,9]. There are multiple clinical diagnostic methods used to support candidiasis diagnoses. Regardless of the detection method (e.g., mass spectrometry, PCR), a microbiological culture step is usually required prior to pathogen identification. This culture step can take between 2-5 days from receipt of a clinical sample (e.g., blood, catheter tip, sputum, urine) to microbiological identification. This long time-to-identification can lead to delays in initiation of optimal antimicrobial chemotherapy. Previous studies have shown relatively poor sensitivity of clinical diagnostics for candidiasis, with a 30-50% false negative rate for blood cultures in patients with autopsy-confirmed cases of candidiasis[10,11]. This demonstrates the limitations for both time and reliability of diagnosis for common existing diagnostic approaches for candidiasis.

Microbial biofilms growing on surfaces of host tissue and medical device materials play an important role in the establishment and maintenance of infections.[15] Bacteria and fungi readily form biofilms, which are often highly resistant to antimicrobial therapy and may disperse to disseminate infection.

Standard culture methods involve significant delay (>24 hours), so faster, culture-free methods are clearly needed to efficiently achieve appropriate antimicrobial therapy.

SUMMARY

The present disclosure provides various fluorescence microscopy based methods and apparatus for rapid, culture free pathogen detection. According to various embodiments, the methods can be performed at a point of care facility rather than at a reference laboratory and can be performed using equipment that does not require extensive training and which, in some cases may be portable. According to various embodiments, the present disclosed methods utilize hyperspectral confocal fluorescence microscopy techniques to identify and characterize pathogens via the detection of unique spectral factors arising from the autofluorescent properties of the pathogens.

DETAILED DESCRIPTION

The present disclosure provides various methods and apparatus for rapid, culture-free pathogen detection. In some embodiments, the method may be label free. According to various embodiments, the presently disclosed methods utilize one or more spectroscopy techniques to identify and characterize pathogens via the detection of unique spectral factors that are specific to particular pathogens.

For the purposes of the present disclosure, the term "rapid" is intended to mean that pathogen detection can take place in a clinical setting on the order of minutes to hours as opposed to current methods which take place on the order of days.

For the purposes of the present disclosure, the term "culture free" is intended to mean that there is no necessary step prior to sample preparation for analysis involving microbiological culture in nutrient medium for the purpose of increasing the number of cells present in the specimen through cell division.

For the purposes of the present disclosure, the term "label free" is intended to mean that the signal to be measured does not require application of exogenous substances that will be the source of signals that serve as markers of the presence or absence of the pathogen in the specimen. For instance, an example of a label would be a fluorescent dye or an enzyme/colorimetric substrate that could be detected as a signal.

According to an embodiment, the present disclosure utilizes hyperspectral confocal fluorescence microscopy (HCFM) to quickly and accurately identify and/or characterize the unique autofluorescence spectra from different pathogens. Accurate identification of a sample is defined as correctly assigning identify of a known control specimen in 80% or more cases. It should be understood that while the description and Examples refer primarily to confocal microscopy, the present disclosure is not necessarily limited to a confocal arrangement. Similarly, while the description and Examples primarily describe the fluorescence microscopy as being "hyperspectral," which commonly refers to the resolution of greater than 100 spectral points, the present disclosure is not necessarily limited to any given number of spectral points and thus includes any embodiment in which information is spectrally-resolved and thus accommodates any level of spectral resolution.

In general, the emission spectra of a sample that is suspected of containing a pathogen is obtained via HCFM and compared to a library of emission spectra from one or more pathogens of interest. According to a specific embodiment, the pathogen of interest may be a *Candida* species. An emission spectra library may be created by culturing various strains of a pathogen of interest, like *Candida* species, and using HCFM and multivariate spectral analysis methods to resolve multiple autofluorescence spectra in the different pathogen strains. The creation of an emission spectra library for three common forms of *Candida* species, namely *C. albicans, C. glabrata*, and *C. parapsilosis*, is described in detail in the Example section below.

Any suitable hyperspectral confocal fluorescence microscope may be used, but according to various embodiments, the HCF microscope should be capable of exciting and detecting the spectral emissions from the autofluorescence at a signal-to-noise ration >3 and possess sufficient spectral resolution to resolve the two autofluorescent spectral emission peaks from each other and other fluorescent signals within the sample (typically, a spectral resolution >=0 nm).

According to an embodiment, a clinical sample (e.g., blood, sputum, urine, catheter tip or other medical device or part thereof) may be obtained from the patient, as appropriate to the type of specimen using standard clinical procedures for obtaining diagnostic specimens. Specimens may then be prepared and directly analyzed using HCFM without the need for initial or additional culturing of the sample and without the need for the addition of any type of label. Sample preparation may involve placing the specimen in buffers or nutrient solutions suitable for HCFM analysis. Emission spectra may be obtained using methods such as those described in the Example section below, except that the sample being analyzed may be a sample obtained in a clinical environment, e.g., from a patient, a device, etc.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

1. S. Magill et al., "Multistate point-prevalence survey of health care-associated infections," N. Engl. J. Med. 27(370), 1198-1208 (2014).
2. N. Yapar, "Epidemiology and risk factors for invasive candidaiasis," J. Ther. Clin. risk Manag. 10, 95-105 (2014).
3. S. R. Lockhart, "Current Epidemiology of *Candida* Infection," Clin. Microbiol. Newsl. 36(17), 131-136 (2014).
4. M. Pfaller and D. Diekema, "Epidemiology of invasive candidiasis: a persistent public health problem," Clin. Microbiol. Rev. 20(1), 133-163 (2007).
5. O. Gudlaugsson et al., "Attributable mortality of nosocomial candidemia, revisited," Clin. Infect. Dis. 37(9), 1172-1177 (2003) [doi:10.1086/378745].

6. F. G. De Rosa et al., "Invasive candidiasis and candidemia: new guidelines," Minerva Anestesiol. 75(7-8), 453-458 (2009).
7. R. P. Wenzel and M. B. Edmond, "The impact of hospital-acquired bloodstream infections," Emerg. Infect. Dis. (7), 174-177 (2001).
8. M. Morrell, V. Fraser, and M. Kollef, "Delaying the Empiric Treatment of *Candida* Bloodstream Infection until Positive Blood Results are Obtained: a Potential Risk Factor for Hospital Mortality," Antimicrob. Agents Chemother. 49(9), 3640-3645 (2005).
9. K. Garey et al., "Time to Initiation of Flucanazole Therapy Impacts Mortality in Patients with Candidemia: A Multi-Institutional Study," Clin. Infect. Dis. 43(1), 25-31 (2006).
10. M Kami et al., "Effect of fluconazole prophylaxis on fungal blood cultures: An autopsy-based study involving 720 patients with haematological malignancy," Br. J. Haematol. 117(1), 40-46 (2002) [doi:10.1046/j.1365-2141.2002.03414.x].
11. J. Berenguer et al., "Lysis-centrifugation blood cultures in the detection of tissue-proven invasive candidiasis disseminated versus single-organ infection," Diagnostic Microbiol. Infect. Dis. 17(2), 102-109 (1993).
12. Antibiotic resistance threats in the United States, 2013. In: (CDC) CfDCaP, editor. Atlanta, Ga. 2013.
13. Freifeld A G, Bow E J, Sepkowitz K A, Boeckh M J, Ito J I, Mullen C A, et al. Clinical practice guideline for the use of antimicrobial agents in neutropenic patients with cancer: 2010 update by the infectious diseases society of America. Clin Infect Dis. 2011; 52(4):e56-93. Epub 2011/01/25. doi: 10.1093/cid/cir073. PubMed PMID: 21258094.
14. McKenzie H, Hayes L, White K, Cox K, Fethney J, Boughton M, et al. Chemotherapy outpatients' unplanned presentations to hospital: a retrospective study. Supportive care in cancer: official journal of the Multinational Association of Supportive Care in Cancer. 2011; 19(7): 963-9. Epub 2010/05/26. doi: 10.1007/s00520-010-0913-y. PubMed PMID: 20499108.
15. Rosa R G, Goldani L Z. Cohort study of the impact of time to antibiotic administration on mortality in patients with febrile neutropenia. Antimicrobial agents and chemotherapy. 2014; 58(7):3799-803. Epub 2014/04/23. doi: 10.1128/AAC.02561-14. PubMed PMID: 24752269; PubMed Central PMCID: PMC4068526.
16. J. D. Walsh et al., "Rapid Intrinsic Fluorescence Method for Direct Identification of Pathogens in Blood Cultures," MBio 4(6), 1-9 (2013) [doi:10.1128/mBio.00865-13.Editor].
17. M. B. Sinclair et al., "Hyperspectral confocal microscope," Appl. Opt. 45(24), 6283-6291 (2006).
18. Z. Khan et al., "Emergence of resistance to amphotericin B and triazoles in *Candida glabrata* vaginal isolates," J. Chemother. 20, 488-491 (2008).
19. A. Panackal et al., "Clinical significance of azole antifungal drug cross-resistance in *Candida glabrata*," J. Clin. Microbiol. 44(5), 1740-1743 (2006).
20. S. Siano and R. Mutharasan, "NADH and flavin fluorescence responses to starved yeast cultures to substrate additions," Biotechnol. Bioeng. 34(5), 660-670 (1989).
21. H. Bhatta and E. M. Goldys, "Characterization of yeast strains by fluorescence lifetime imaging microscopy," FEMS Yeast Res. 8(1), 81-87 (2008) [doi:10.1111/j.1567-1364.2007.00340.x].
22. A. Kindzelskii and H. R. Petty, "Fluorescence spectroscopic detection of mitochondrial flavoprotein redox oscillations and transient reduction of the NADPH oxidase-associated flavoprotein in leukocytes," Eur. Biophys. J. 33(4), 291-299 (2004) [doi:10.1007/s00249-003-0361-4].
23. G. Borekci et al., "Identification Of *Candida* Species From Blood Cultures With Fluorescent In Situ Hybridization (fish), Polymerase Chain Reaction-restriction Fragment Length Polymorphism (per-rflp) And Conventional Methods," Med. J. Trak. Univ. 27(2), 183-191 (2009) [doi:10.5174/tutfd.2009.01700.1].
24. S. Silva et al., "*Candida glabrata, Candida parapsilosis* and *Candida tropicalis*: biology, epidemiology, pathogenicity and antifungal resistance," FEMS Microbiol. Rev. 36(2), 288-305 (2012).
25. H. D. T. Jones et al., "Preprocessing strategies to improve MCR analyses of hyperspectral images," Chemom. Intell. Lab. Syst. 117, 149-158, Elsevier B. V. (2012) [doi:10.1016/j.chemolab.2012.01.011].
26. J. Ohlhausen et al., "Multivariate statistical analysis of time-of-flight secondary ion mass spectrometry images using axsia," Appl. Surf. Sci. 231-232, 230-234 (2004).
27. J. Schoonover, R. Marx, and S. Zhang, "Multivariate curve resolution in the analysis of vibrational spectroscopy data files," Appl. Spectrosc. 57(5), 154A-170A (2003).
28. R. Davis et al., "Accurate detection of low levels of fluorescence emission in autofluorescent background: *Francisella* infected macrophage cells," Microsc. Microanal. 16(4), 478-487 (2010).
29. W. Vermass et al., "In vivo hyperspectral confocal fluorescence imaging to determine pigment localization and distribution in cyanobacterial cells," PNAS 105(10), 4050-4055
30. Graus, M S, Timlin, J A and Neumann, A K, "Hyperspectral fluorescence microscopy detects autofluorescent factors that can be exploited as a diagnostic method for *candida* species differentiation," Journal of Biomedical Optics, 2017, 22:1, 016002. (PMC5216876).

Example I

Differentiation of *Candida* Species Using Hyperspectral Fluorescence Microscopy Materials and Methods Yeast Growth/Preparation. Lab strain yeasts of *C. albicans, C. glabrata*, and *C. parapsilosis* were grown for the purpose of ascertaining if the individual *Candida* species have unique autofluorescence characteristics. *C. albicans* (ATCC, MYA-2876), *C. glabrata* (ATCC, 2001), and *C. parapsilosis* (ATCC, 22019) were grown in human serum (EMD Millipore, S1) for 16 hrs at 37° C. in an orbital shaker at 250 rpm. Each of the *candida* species were then put on individual microscope slides and sealed with nail polish.

Hyperspectral Confocal Fluorescence Microscopy. A custom built hyperspectral confocal fluorescence microscope was used to acquire the autofluorescent emissions from the samples. Previous work describes the methodology for image acquisition using the custom built microscope[17]. See also Graus et al, "Hyperspectral fluorescence microscopy detects autofluorescent factors that can be exploited as a diagnostic method for *candida* species differentiation," Journal of Biomedical Optics, 2017."[30] In summary, a 488 nm laser (Coherent, Inc. Sapphire) and a 60× apochromat objective (Olympus Plan Apochromat, NA 1.4) were used to excite fluorescence from a diffraction-limited spot. The laser power was ~80 µW at the entrance to the microscope and the integration time is 0.2 ms/pixel. To detect fluorescent emissions a prism spectrometer coupled to an electron multiplying charged coupled device (EMCCD) camera (Andor Technologies, Inc., iXon) was used.

Spectral Analysis. All images were preprocessed to remove known spectral artifacts introduced by the imaging system (cosmic ray spikes, detector offset, and structured dark noise)[25], as well as calibrate the wavelength axis. The resulting individual spectral images were combined into three composite image data sets, one for each *Candida* species. Multivariate Curve Resolution (MCR) was performed on each of these composite data sets to develop a spectral model that described more than 98% of the spectral variance. The MCR algorithm has been described previously[26,27] and has demonstrated success in exploratory analysis to identify underlying spectral components from multicomponent biological systems[28,29]. The MCR results identified near-identical spectral components regardless of the yeast species, therefore a combined spectral model for all three species was deemed appropriate. This combined model was generated by performing MCR on a combined set of images from all three species and described >96% of the spectral variance in the data. Classical Least Squares (CLS) prediction was used to determine the location and abundance of each spectral component in the spectral images. Images corresponding to the location and abundance of individual spectral components were exported as Tif files for subsequent image processing. Although the spectral signatures were virtually identically for all three *Candida* species, these images clearly indicate their location and abundance was not.

Feature Selection. Fiji (ImageJ) was used to threshold and quantify features from the images. A threshold of three standard deviations above background intensity was used to extract features for all emission factors. The features quantified for each emission factor were; total and average intensity per feature, average intensity variance per feature, total and average number of features per cell, and total and average area of features.

Classification. The above were then input into a classification tree algorithm. A classification tree analysis was developed in Matlab using the statistics and machine learning toolbox (Mathworks, version 2015a). To test the performance of the classifier, we divided the data into a training group of 337 cells and a test group of 37 cells (composed of 10% of each species population). To validate the accuracy of the classification tree we measured three statistics: cross validation error, resubstitution error, and the true predictive error for six levels of tree pruning using the training set. To calculate the true error of prediction the number of misclassifications in the test set was divided by the total number of samples in the training set. All data presented was pooled from triplicate biological replicates of samples.

Results

Figure 1:
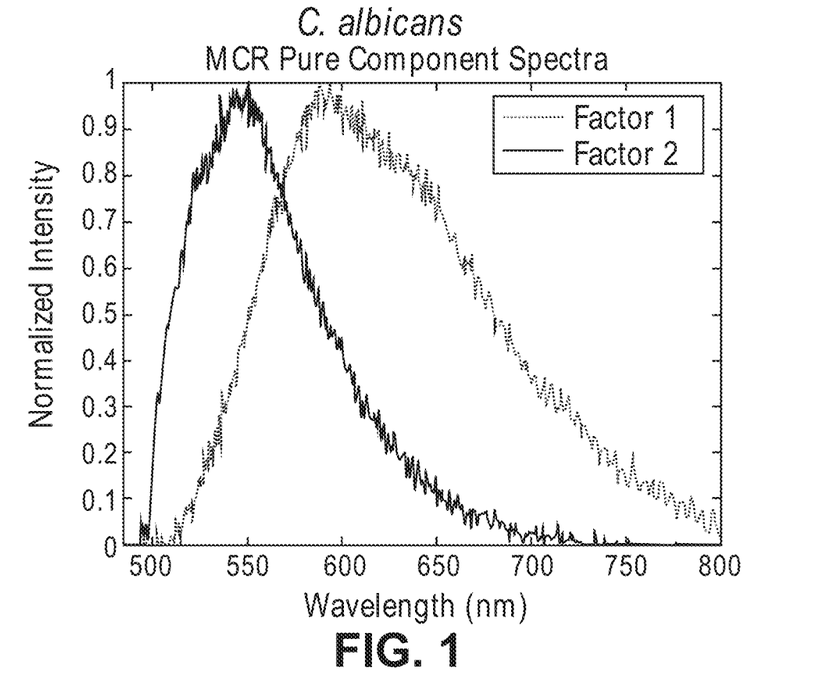
FIG. 1 shows two emission spectra of *C. albicans* derived from MCR analysis after 16 hours of incubation. Fungal emission spectra are composed from >80 cells.
Figure 2:
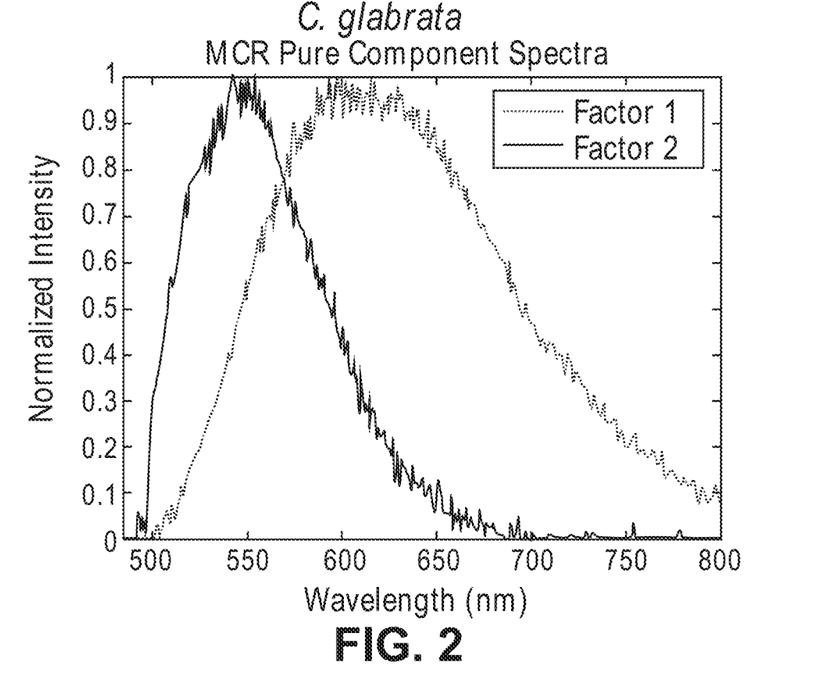
FIG. 2 shows two emission spectra of *C. glabrata* derived from MCR analysis after 16 hours of incubation. Fungal emission spectra are composed from >80 cells.
Figure 3:
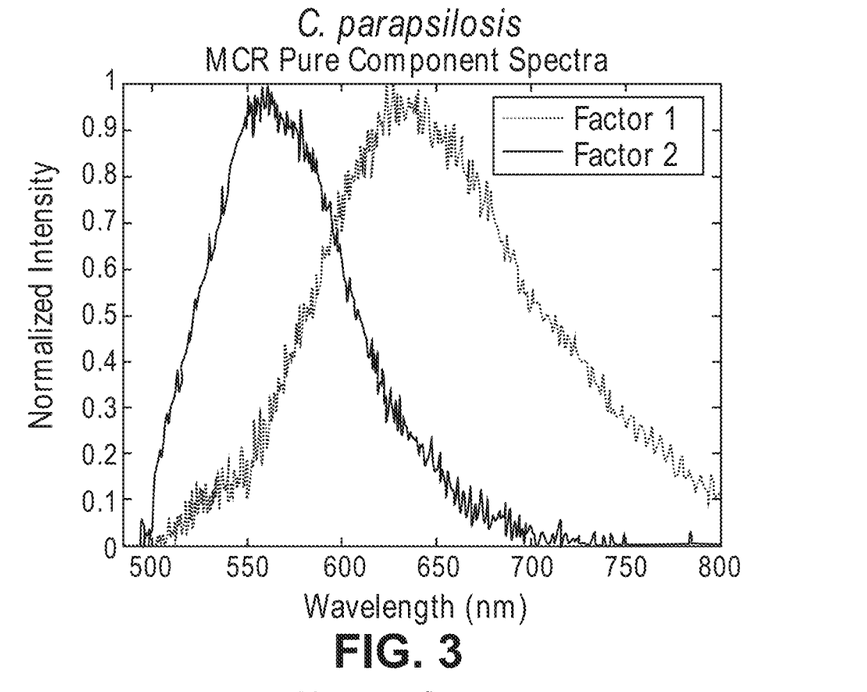
FIG. 3 shows two emission spectra of *C. parapsilosis* derived from MCR analysis after 16 hours of incubation. Fungal emission spectra are composed from >80 cells.
Figure 4:
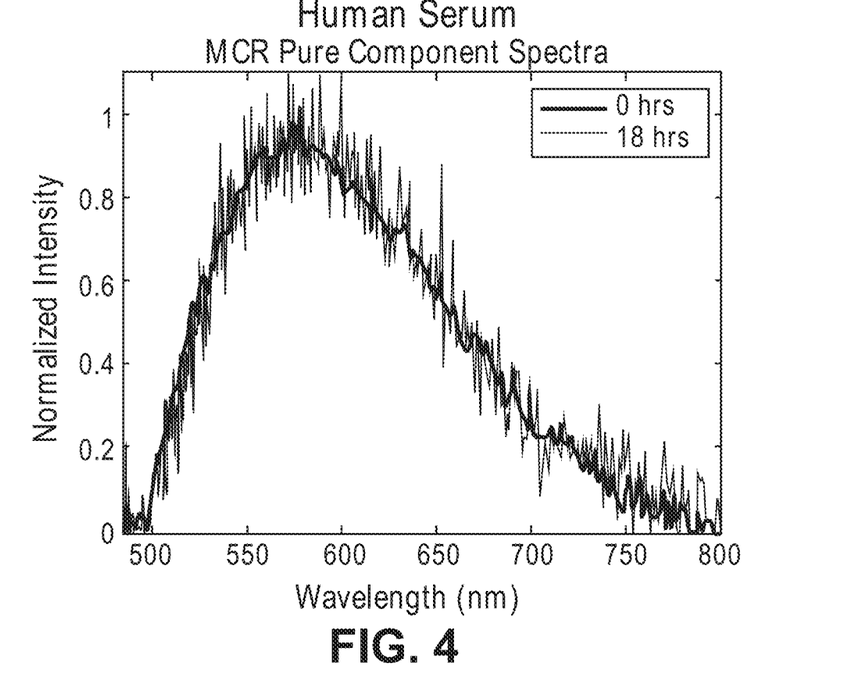
FIG. 4 shows emission spectra of human serum at 0 hour incubation and 18 hours of incubation to demonstrate that emission factors found in *Candida* samples in FIGS. 1-4 are not due to emission of human serum.
Figure 5A:
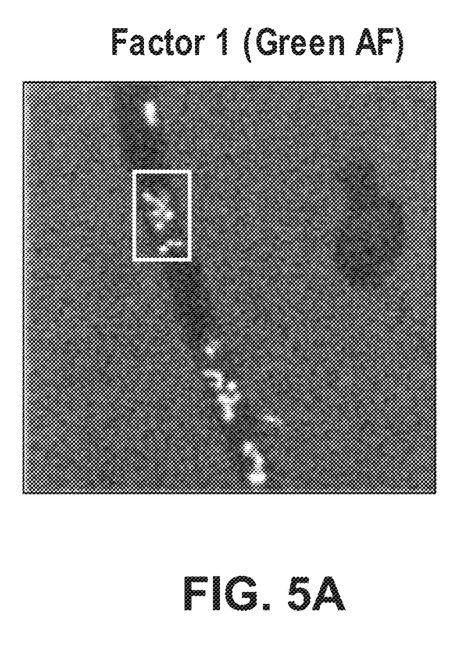
FIG. 5A is a representative image of the green autofluorescence factor of *C. albicans*. The box highlights autofluorescent features within the fungal cells.
Figure 5B:
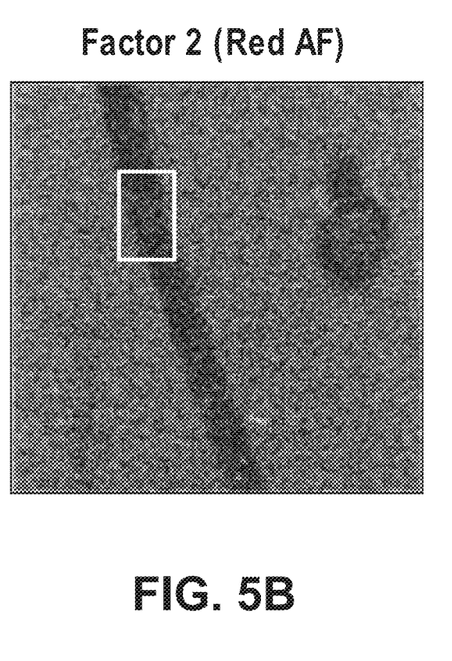
FIG. 5B is a representative image of the red autofluorescence factor of *C. albicans*. The box highlights autofluorescent features within the fungal cells.
Figure 6A:
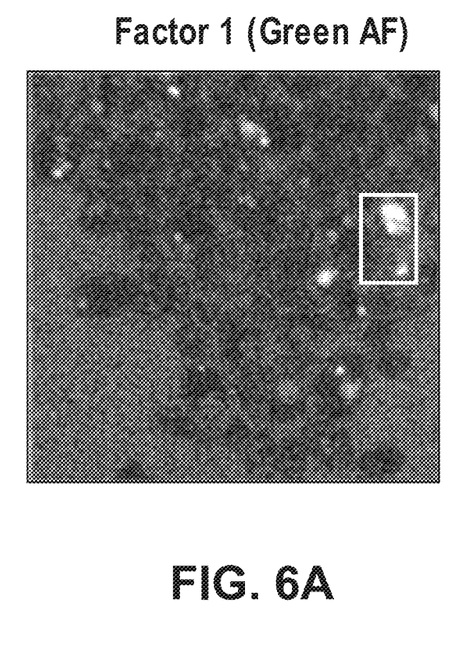
FIG. 6A is a representative image of the green autofluorescence factor of *C. glabrata*. The box highlights autofluorescent features within the fungal cells.
Figure 6B:
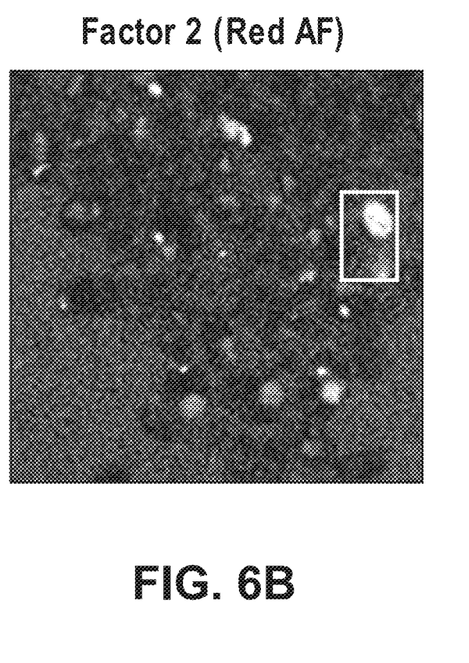
FIG. 6B is a representative image of the red autofluorescence factor of *C. glabrata*. The box highlights autofluorescent features within the fungal cells.
Figure 7A:
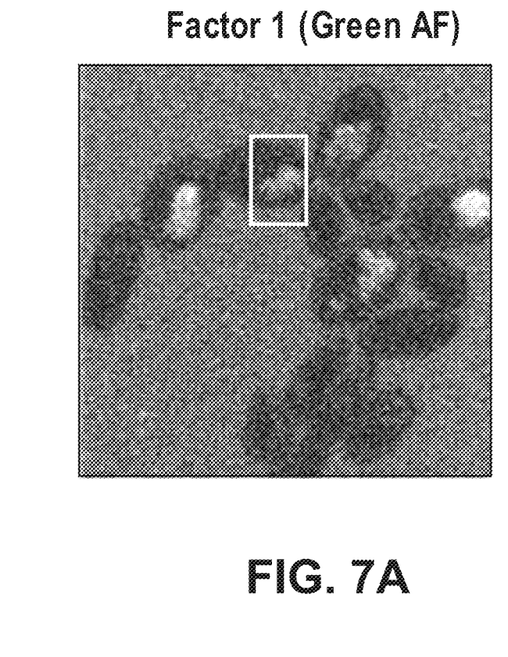
FIG. 7A is a representative image of the green autofluorescence factor of *C. parapsilosis*. The box highlights autofluorescent features within the fungal cells.
Figure 7B:
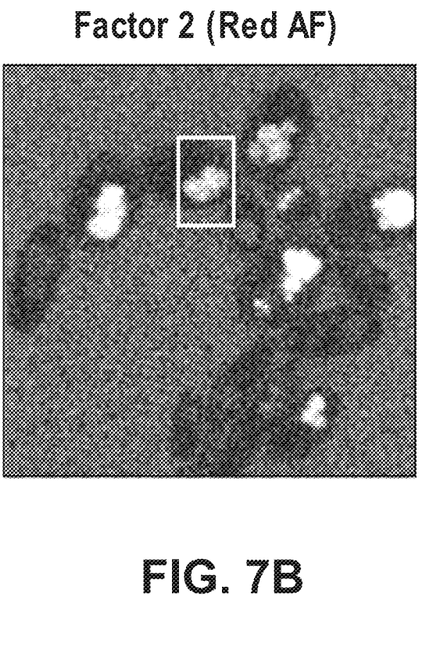
FIG. 7B is a representative image of the red autofluorescence factor of *C. parapsilosis*. The box highlights autofluorescent features within the fungal cells.

In these studies, we used a pooled human serum for growth because of its similarity to the growth condition of fungal pathogens in peripheral blood. The MCR analysis resulted in two different emission factors for all species (FIGS. 1-3) and a linear offset arising from the detector electronics (not shown). Factor 1's spectral shape and peak (550 nm) are very similar across all species, leading to the idea that the three species investigated share a set of common autofluorescent molecules that emit around 550 nm. In contrast, factor 2's spectral shape and peak (600-650 nm) vary slightly depending on which species is being observed (FIG. 1A-C). For example, *C. albicans* factor 2 peak is found at 600 nm and *C. parapsilosis* factor 2 peak is found at 650 nm, and interestingly *C. glabrata* factor 2 peak is broad (the peak encompasses 600-650 nm). When we examined autofluorescent emission from human serum alone, it did not match either factor found in the *Candida* samples and is not an obvious linear combination of the two factors (FIG. 4).

Along with the spectral factors, the MCR analysis also returns concentration maps that indicate the relative abundance of each spectral factor. In order to determine if the spatial localizations of autofluorescence emissions were similar, we quantified multiple spatial and spectral characteristics of each of the autofluorescence signatures from the features within the hyperspectral confocal fluorescence images (FIGS. 5A, 5B, 6A, 6B, 7A, 7B). In the case of *C. albicans* we found very small features mostly composed of factor 1 that were on average around 0.42 $\mu m^2$. For *C. parapsilosis* we observed large features primarily composed of factor 2 that are on average around 1 $\mu m^2$. However, features in *C. glabrata* images contained both factor 1 and factor 2 with an average area around 0.27 $\mu m^2$ and 0.67 $\mu m^2$ respectively. Remarkably, the majority of autofluorescence from *C. parapsilosis* comes from factor 2. Mean factor 2 intensity of the *C. parapsilosis* features was 2 fold greater than *C. glabrata* features and 10 fold greater than *C. albicans* features. These differences in autofluorescence emission geometry as well as other autofluorescence characteristics allowed us to create a classifier from the spatial and spectral features of the autofluorescence emission that are unique to individual species.

Figure 8:
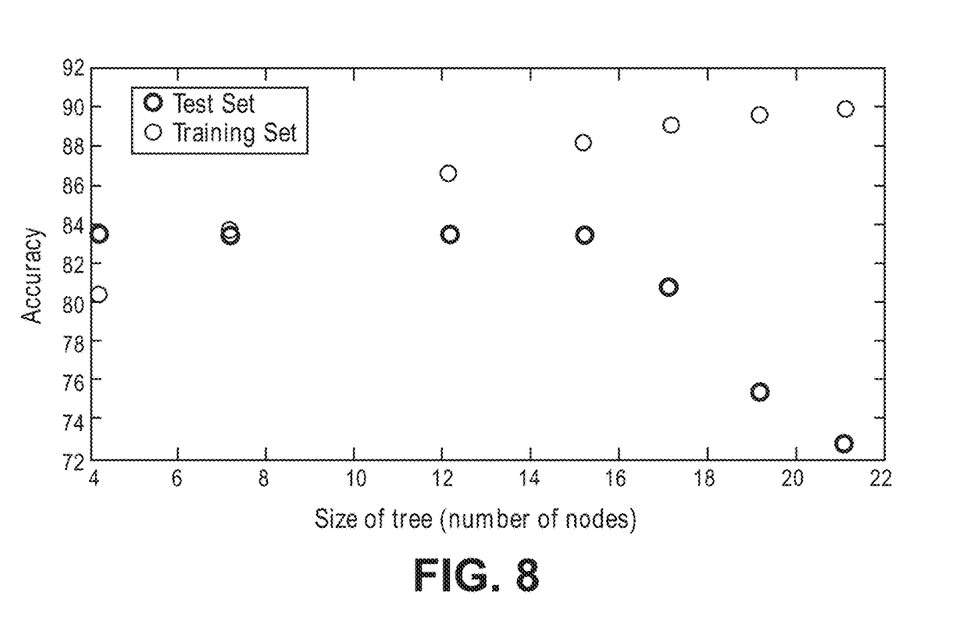
FIG. 8 shows classification tree pruning and demonstrates that over-fitting decreases the accuracy of the classification tree for the test set. The pruning level for classification tree was chosen by the divergence of the test set and training set which corresponds with pruning level 4 (i.e. a 12 node classification tree).
Figure 9:
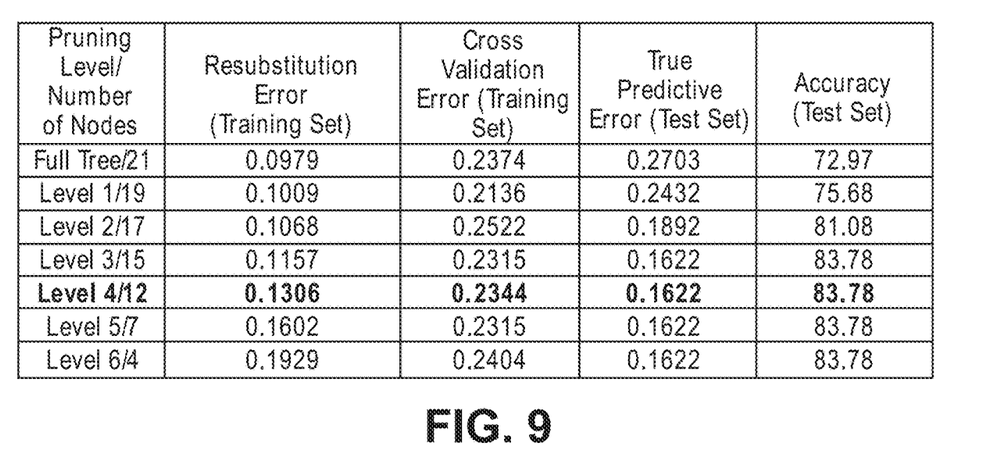
FIG. 9 is a table displaying statistics for the different pruning levels of the classification tree. Bold statistics indicate chosen level for prediction analysis of the test set.
Figure 10:
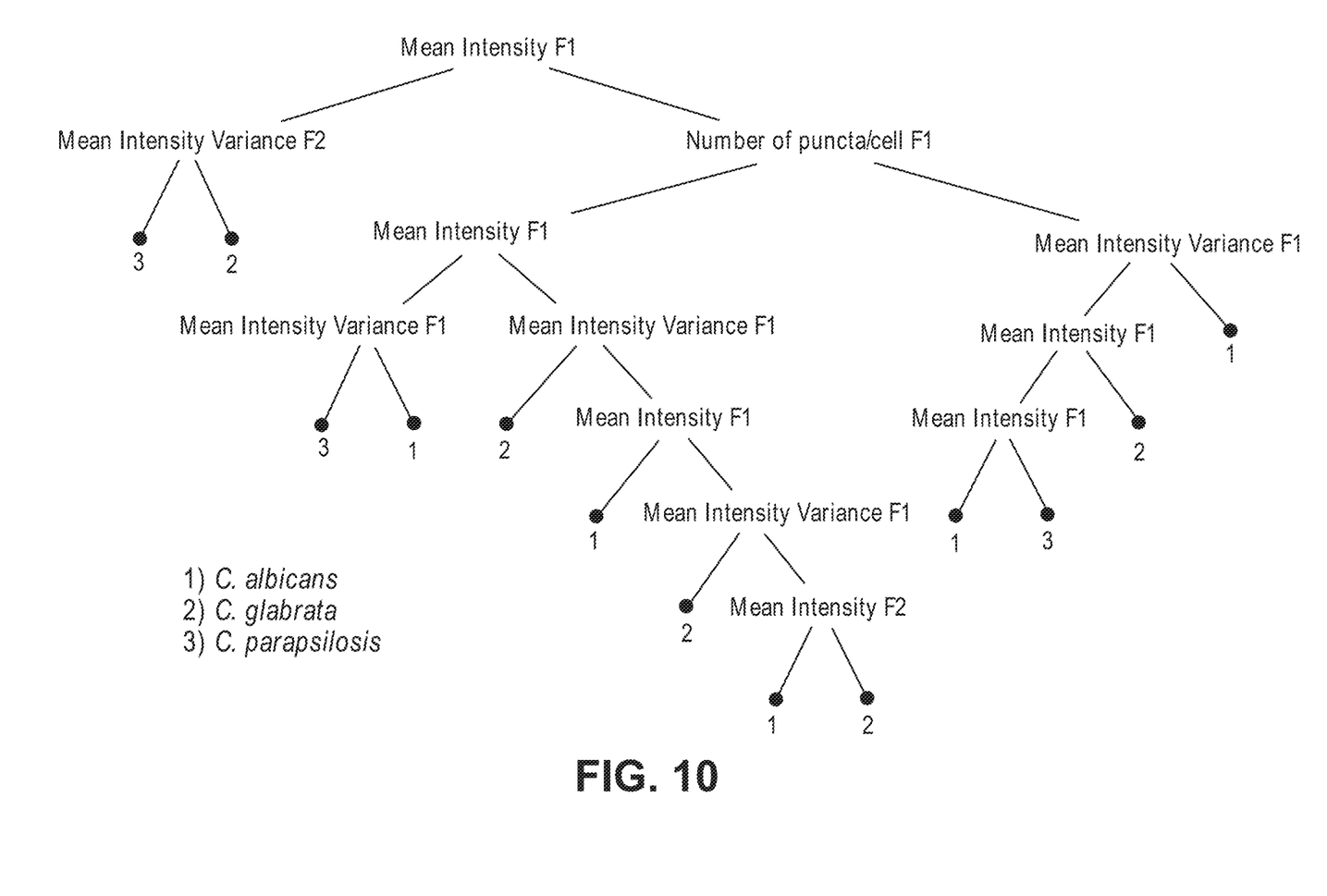
FIG. 10 demonstrates that feature characteristics are used to accurately predict species. The pruned classification tree indicates that factor 1 characteristics are crucial for accurate species identification.

We developed a classification tree from these spectral and spatial features and the accuracy of this classification was measured using three statistics for six levels of pruning using the training set and test set. The accuracy of both the training set and test set are plotted (FIGS. 8, 9). The statistics and accuracy plot revealed some of the less pruned classification trees (i.e. larger classification trees) have a lower true predictive error, demonstrating that the full classification tree may have been overfitting and that the predictions reflected noise or outliers. Based on these results we selected level 4 as the optimal pruning level (point at which the training and test set accuracies diverge in FIG. 8). With this optimal tree we were able to achieve 84% accurate species identification from the test set of data (FIG. 9). We were also able to observe which autofluorescent characteristics were used to construct the classification tree (FIG. 10). Interestingly, in this predictive model, factor 1 autofluorescent characteristics are more important than factor 2 characteristics for predicting the *Candida* species. We then calculated the predictive accuracy for identifying each species in the independent test set. The classification tree was able to predict 75% of *C. albicans* samples accurately, 88% of *C. glabrata* accurately, and 83% of *C. parapsilosis* accurately. On closer inspection of the results, it was found that *C. albicans* was misidentified twice, once with *C. glabrata* and once with *C. parapsilosis*. Whereas, *C. glabrata* was found to only be misidentified with *C. parapsilosis* and *C. parapsilosis* misidentified with *C. glabrata*.

Discussion

*Candida* species are well known for their ability to cause morbidity and mortality. It is also known that some species, such as *C. glabrata*, have intrinsic resistances to azole based anti-fungal drugs[18,19]. Due to this it is important to be able to quickly and accurately identify the pathogenic fungal species prior to administering treatment. The method we describe in this study takes advantage of the spatial and spectral resolution of HCFM. The ability to characterize the unique autofluorescence spectra in the different *Candida* species coupled with their spatial localizations has allowed for species level identification of *Candida* species yeasts grown in conditions that closely mimic pathological conditions and commonly available clinical specimen types. Yeasts are known to emit autofluorescence under appropriate conditions due to native fluorophores, such as flavins[20]. Flavins and flavoproteins likely contribute to the fungal autofluorescence that we observed. Flavin compounds emit around 530 nm from 460 nm excitation[21], which matches closely with our factor 1 peak wavelength and our excitation line. Flavin molecules also associate with the plasma membrane, intracellular granules, and mitochondria[22]. We did not observe any autofluorescent signatures around the plasma membrane, but we did observe intracellular signatures for factor 1. For both *C. albicans* and *C. glabrata* we detected small features for factor 1 leading to the possibility that we observed flavin molecules either in intracellular granules or mitochondria. Interestingly, when observed, factor 1 tended to be smaller in size than factor 2. Also, Factor 1 tended to be located inside areas that also contained factor 2, leading us to speculate that factor 2 may be another native fluorophore, yet to be described, that occupies a similar subcellular compartment.

Previous studies have shown that by utilizing a single excitation source coupled with a monochromator and correlating microbial sample type with the intensity of emission at several wavelengths, it was possible to discriminate bacterial and fungal species[16]. In contrast, our approach uses the entire emission spectrum from 500-850 nm to identify multiple component spectra in the specimens. Our results also extend earlier approaches by measuring autofluorescence events at the individual cell level, whereas other methods use a population or ensemble-based approach and measure the overall autofluorescence signature of a population of cells. Finally, our approach utilizes identifying information from the subcellular spatial distribution of autofluorescence signals. Other molecular methods such as FISH (Fluorescent In Situ Hybridization) have been described both as quick and accurate[23]. However, utilizing FISH requires that each species needing identification has its own unique probe as well as preparing the sample in such a way that the probe can enter the cell and a culture step to generate enough sample to work with. Because our method does not require large numbers of cells and is a label-free method, it may be useable on a minimally processed clinical specimen, perhaps even as a point of care diagnostic. By utilizing autofluorescent emission characteristics the classification tree is able to accurately predict the *Candida* species, demonstrating the robustness of the procedure as a quick and accurate identification method.

What is claimed is:

1. A method for rapid, culture-free pathogen detection comprising:
    obtaining a sample suspected of containing a pathogen,
    preparing the sample for analysis via fluorescence microscopy (FM); wherein preparation does not include culturing the sample;
    analyzing the sample via FM to analyze autofluorescence events from individual cells in the sample and produce a fluorescence spectral image comprising a plurality of spectral factors;
    deconvolving the fluorescence spectral image to identify a subset of the plurality of spectral factors wherein the subset provides differentiation between different species of the same pathogen; wherein deconvolving comprises:
        preprocessing the spectral image to remove known spectral artifacts; and
        employing multivariate curve resolution (MCR); and
    comparing the identified subset of spectral factors to a known library of spectral factors that indicate the presence and species of the pathogen; and
    determining whether the sample contains the pathogen based on the comparison of the identified spectral factors to the known spectral factors;
    wherein the pathogen is a *Candida* species.

2. The method of claim 1 wherein the identified spectral factors enable differentiation between species of the same pathogen within the same sample in a single analytical step.

3. The method of claim 1 wherein the spectral factors enable differentiation between *C. albicans*, *C. glabrata*, and *C. parapsilosis*.

4. The method of claim 1 wherein preparation also does not include labeling the sample.

5. The method of claim 1 wherein the FM is confocal.

6. The method of claim 1 wherein the FM is hyperspectral.

7. The method of claim 1 wherein the FM analyzes an emissions spectrum from 500-850 nm.

8. The method of claim 1 wherein the deconvolved spectral image further indicates a location and abundance of different species of the same pathogen within the sample.

9. A method for rapid, label-free pathogen detection comprising:
    obtaining a sample suspected of containing a pathogen,
    preparing the sample for analysis via fluorescence microscopy (FM); wherein preparation does not include labeling the sample;
    analyzing the sample via FM to analyze autofluorescence events from individual cells in the sample and produce a fluorescence spectral image comprising a plurality of spectral factors;
    deconvolving the fluorescence spectral image to identify a subset of the plurality of spectral factors wherein the subset provides differentiation between different species of the same pathogen; wherein deconvolving comprises:
        preprocessing the spectral image to remove known spectral artifacts; and
        employing multivariate curve resolution (MCR); and
    comparing the identified subset of spectral factors to a known library of spectral factors that indicate the presence and species of the pathogen; and
    determining whether the sample contains the pathogen based on the comparison of the identified spectral factors to the known spectral factors;
    wherein the pathogen is a *Candida* species.

10. The method of claim 9 wherein the spectral factors enable differentiation between species of the same pathogen within the same sample in a single analytical step.

11. The method of claim 9 wherein the spectral factors enable the differentiation between *C. albicans*, *C. glabrata*, and *C. parapsilosis*.

12. The method of claim 9 wherein the FM is confocal.

13. The method of claim 9 wherein the FM is hyperspectral.

14. The method of claim 9 wherein the FM analyzes an emissions spectrum from 500-850 nm.

15. The method of claim 9 wherein the deconvolved spectral image further indicates a location and abundance of different species of the same pathogen within the sample.

* * * * *